United States Patent
DeLegge

(12) 
(10) Patent No.: US 8,043,260 B2
(45) Date of Patent: *Oct. 25, 2011

(54) GASTRIC ACCESS PORT

(75) Inventor: Rebecca DeLegge, Mt. Pleasant, SC (US)

(73) Assignee: Delegge Medical, Inc., Mount Pleasant, SC (US)

(*) Notice: Subject to any disclaimer, the term of this patent is extended or adjusted under 35 U.S.C. 154(b) by 158 days.

This patent is subject to a terminal disclaimer.

(21) Appl. No.: 12/313,219

(22) Filed: Nov. 17, 2008

(65) Prior Publication Data

US 2009/0082736 A1    Mar. 26, 2009

Related U.S. Application Data

(63) Continuation of application No. 11/091,153, filed on Mar. 28, 2005, now Pat. No. 7,452,347, which is a continuation of application No. 09/929,913, filed on Aug. 15, 2001, now Pat. No. 6,872,189.

(60) Provisional application No. 60/225,530, filed on Aug. 15, 2000.

(51) Int. Cl.
*A61M 29/00* (2006.01)
*A61M 5/32* (2006.01)

(52) U.S. Cl. ............ 604/104; 604/178; 604/910

(58) Field of Classification Search .......... 604/104–109, 604/174, 175, 178, 173, 180, 910, 164.04, 604/93.01, 523; 128/DIG. 26
See application file for complete search history.

(56) References Cited

U.S. PATENT DOCUMENTS

| | | | | |
|---|---|---|---|---|
| 2,010,417 | A | * | 8/1935 | Schwab ............ 604/257 |
| 3,926,187 | A | | 12/1975 | Iglesias |
| 4,306,545 | A | | 12/1981 | Ivan et al. |
| 4,390,017 | A | | 6/1983 | Harrison et al. |
| 4,417,890 | A | | 11/1983 | Dennehey et al. |
| 4,424,833 | A | | 1/1984 | Spector et al. |
| 4,473,369 | A | | 9/1984 | Leuders et al. |
| 4,557,261 | A | | 12/1985 | Ruegheimer |
| 4,774,944 | A | | 10/1988 | Mischinski |
| 4,826,477 | A | * | 5/1989 | Adams ............ 604/4.01 |

(Continued)

FOREIGN PATENT DOCUMENTS

EP    0 976 418 A1    2/2000

(Continued)

OTHER PUBLICATIONS

Japan Patent Office, Office Action in Japanese Patent Application No. 2002-519038, mailed Sep. 1, 2010.

*Primary Examiner* — Matthew F DeSanto
(74) *Attorney, Agent, or Firm* — Kenyon & Kenyon LLP

(57) ABSTRACT

An improved mechanism for attaching a feeding tube to a feeding delivery system is presented. The feeding delivery system is attached to an elongated connecting member that is pivotally attached to a bolster. After attachment, the elongated connecting member is rotated to engage another tube at the base of the pivot. Before pivoting, the passageway is blocked by the interference of the elongated connecting member. As the elongated connecting member is rotated, the conduit system aligns and becomes a passageway to and from the stomach. The device provides a three part rigid plastic fit that does not wear out over a number of uses. The device prevents splash events, which occur when a feeding adapter is opened or when the adapter or valve is forced open by a cough or gastric pressure build up.

16 Claims, 2 Drawing Sheets

U.S. PATENT DOCUMENTS

| | | | |
|---|---|---|---|
| 4,834,712 A | 5/1989 | Quinn et al. | |
| 4,863,438 A | 9/1989 | Gauderer et al. | |
| 4,944,732 A | 7/1990 | Russo | |
| 5,007,900 A | 4/1991 | Picha et al. | |
| 5,026,352 A | 6/1991 | Anderson | |
| 5,065,909 A * | 11/1991 | Pino et al. | 222/484 |
| 5,100,394 A | 3/1992 | Dudar et al. | |
| 5,158,569 A | 10/1992 | Strickland et al. | |
| 5,259,399 A | 11/1993 | Brown | |
| 5,267,983 A | 12/1993 | Oilschlager et al. | |
| 5,290,250 A | 3/1994 | Bommarito | |
| 5,339,982 A | 8/1994 | Tardie | |
| 5,342,321 A | 8/1994 | Potter | |
| 5,458,583 A | 10/1995 | McNeely et al. | |
| 5,488,949 A | 2/1996 | Kreifels et al. | |
| 5,549,657 A * | 8/1996 | Stern et al. | 604/537 |
| 5,720,734 A | 2/1998 | Copenhaver et al. | |
| 5,836,924 A | 11/1998 | Kelliher et al. | |
| 6,095,997 A | 8/2000 | French et al. | |
| 6,419,699 B1 | 7/2002 | Schuessler | |
| 6,872,189 B2 * | 3/2005 | DeLegge | 604/104 |
| 7,452,347 B2 * | 11/2008 | DeLegge | 604/104 |

FOREIGN PATENT DOCUMENTS

| | | |
|---|---|---|
| JP | 1531605 U | 12/1926 |
| JP | 11505731 T | 5/1999 |
| JP | 2002540909 T | 12/2002 |
| WO | 9636378 A1 | 11/1996 |
| WO | 0032260 A1 | 6/2000 |

* cited by examiner

GASTRIC ACCESS PORT

The present application is a continuation of U.S. patent application Ser. No. 11/091,153, filed Mar. 28, 2005 now U.S. Pat. No. 7,452,347, which in turn is a continuation of U.S. patent application Ser. No. 09/929,913, filed Aug. 15, 2001, now U.S. Pat. No. 6,872,189, said patent application claiming priority of U.S. Provisional Patent Application No. 60/225,530, which was filed Aug. 15, 2000, all of the above being incorporated herein by reference.

FIELD OF THE INVENTION

This invention relates to devices and methods for feeding through gastrostomy feeding or access ports.

BACKGROUND OF THE INVENTION

Gastrostomy feeding devices connect the stomach to the exterior of the body through a stoma site. These devices are inserted and left in for the period of time that access to the stomach is needed, and are used as a conduit for feeding, decompression, delivery of medications, and suctioning of fluids. Gastrostomy feeding ports may rise just above the skin level, or they may be an extended tube-like structure with adapters on the exterior end. In either case, an external bolster is used to hold the tube in place to prevent slippage of the external portion of the tube into the stomach.

Bolsters in the prior art not only provide a mechanism to hold the tube to prevent tube slippage, but also in the tubes that rise just slightly above the skin, these bolsters are charged with connecting to the feeding delivery sets, or syringes used to access the gastrostomy. In this case, a part of the bolster must connect the lumen that traverses the stoma into the stomach with the feeding set or syringe. When this connection is opened, reflux of gastric contents is likely.

Prevention of the leakage of gastric contents and the control of gastric pressures in an acidic environment has become a significant design challenge. Materials must be resilient, soft and resealable over time. Unfortunately, many of the gastrostomy feeding port valves or mechanisms for reflux prevention have failed over time, especially after repeated uses.

Valves have been used as a mechanism to block the unwanted flow of gastric contents outward. The prior art includes check valves, such as those available commercially by Novartis under Russo, U.S. Pat. No. 4,944,732. This product offers a replacement valve which may be screwed into place. The Button, another commercially available device, offers an external rubber flip cap and a tongue valve placed in the stomach end of the communicating lumen. Over time, both the rubber flip cap and the tongue valve become embrittled, and will fail to function.

Copenhaver, et al. U.S. Pat. No. 5,720,734, commercially available as the Passport from Wilson-Cook Medical, Inc., discusses an "s" slit valve, which lies under compression in a rigid plastic lumen. Because it is a rubber valve, it is fraught with the same embrittlement issues, especially after being violated multiple times per day over a long period.

Prior art devices are formed of rigid plastic and fit only feeding delivery set tips and use an adapter to fit the bolus syringe tips, or have been soft rubber or plastic and subject to breakage upon repeated usage. There is a need for a long term indwelling gastrostomy feeding port which does not utilize a soft rubber valve system or soft rubber flip caps, but which serves to control flow to and from the stomach. This required device eliminates the need for rubber valves and rubber flip caps.

SUMMARY OF THE INVENTION

A connecting member is housed within a bolster of rigid or soft plastic or rubber. The connecting member pivots about a point which is located at one end of the connecting member. A lumen is connected to the stomach downstream of the pivot point. The lumen is closed when the connecting member is closed and inactive. In the closed or inactive position, the connecting member is substantially perpendicular to the lumen connecting the stomach. The connecting member in the inactive state blocks the flow of the lumen by physically obstructing the flow path.

Before activating the connecting member, the feeding delivery set or syringe is placed into the lumen of the connecting member. This lumen engages the tip of the feeding delivery set tip or syringe as it is the matching taper and provides a plastic-to-plastic fit. To activate, the connecting member is pivoted substantially 90 degrees and the lumen is open. Once the desired procedure of delivering or withdrawing solutions is accomplished, the connecting member is pivoted back into horizontal position and renders the lumen inactive.

By one aspect of the present invention, here is provided a long-term indwelling catheter with an improved anti-reflux mechanism, which remains sealed over multiple uses. The improved anti-reflux mechanism is useful to any feeding gastrostomy system that is left indwelling in a patient and used repeatedly on a daily basis.

The pivoting connecting member may be formed of rigid plastic materials housed in a matrix of a rigid or a resilient bolster connecting the lumen of the feeding tube. The pivoting connecting member is inactive and blocking the lumen of the feeding tube when it is at rest. Upon connection to a syringe or feeding delivery set, the pivoting connecting member is rotated 90 degrees until it is aligned with the feeding lumen. Additional embodiments include the plastic to plastic fit and taper of the pivoting connecting lumen to the feeding delivery sets and to the feeding bolus syringe tip, thus avoiding the use of adapters for engagement.

DETAILED DESCRIPTION OF THE INVENTION

Figure 1:
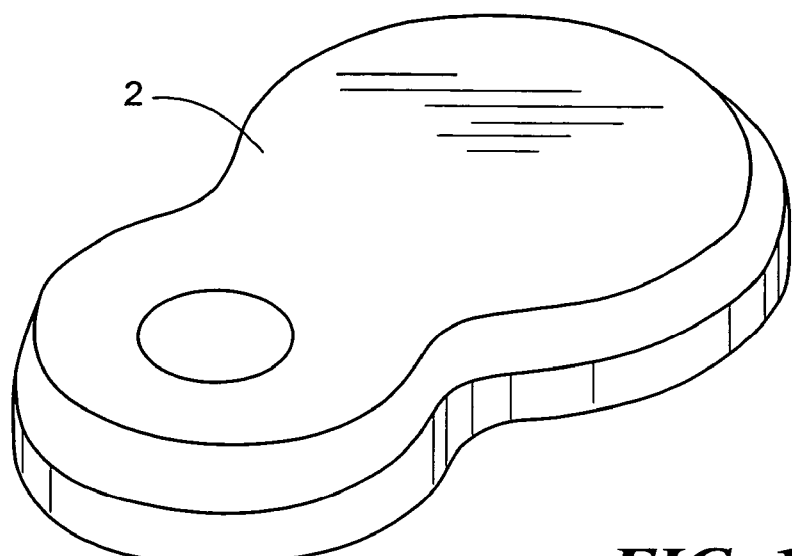
FIG. 1 is a perspective view of the device showing the bottom of the bolster in which the pivoting connecting tube is housed.
Figure 2:
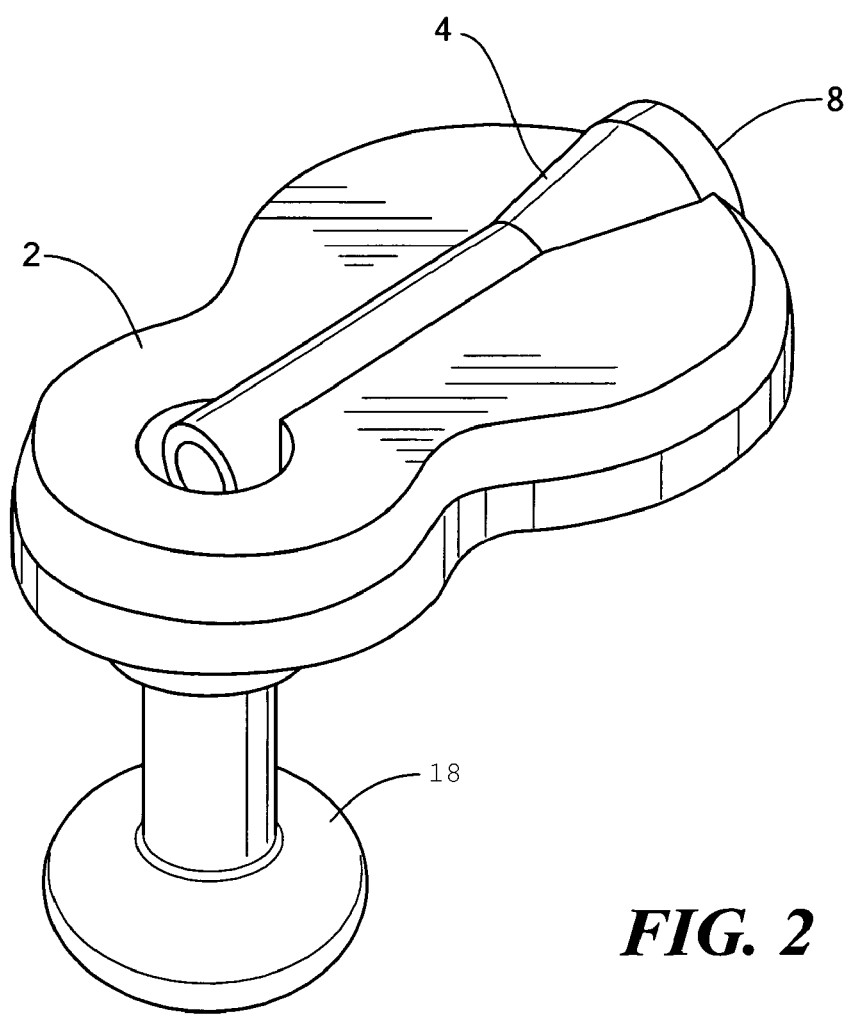
FIG. 2 is a perspective view of the device showing the top of bolster in which the pivoting connecting tube is housed.

Referring now to the drawing Figures, FIGS. 1 and 2 show an anchoring device such as bolster 2 which forms a housing for a connecting member 4. The bolster may be formed of various materials. It is preferred that the bolster be formed of rigid or soft plastic material, or of rubber. The bolster should be formed of materials which are easy to clean, do not readily oxidize, and do not promote the growth of bacteria.

As shown in FIG. 2, the connecting member is housed within the bolster. One end 8 of the connecting member is preferred to extend beyond the bolster, so that the bolster may be connected to a feeding tube, a syringe or other delivery device, without the necessity of pivoting or rotating the connecting member, so that the device remains in the closed position during connection.

The opposite end of the connecting member is attached to the bolster by means of a pivotal connection. Accordingly, the connecting member may be connected or rotated relative to the bolster. When the connecting member is in the position shown in FIG. 2, the device is in the closed, or inactive position. That is, access to the stomach through the lumen is blocked by the connecting member.

Figure 3:
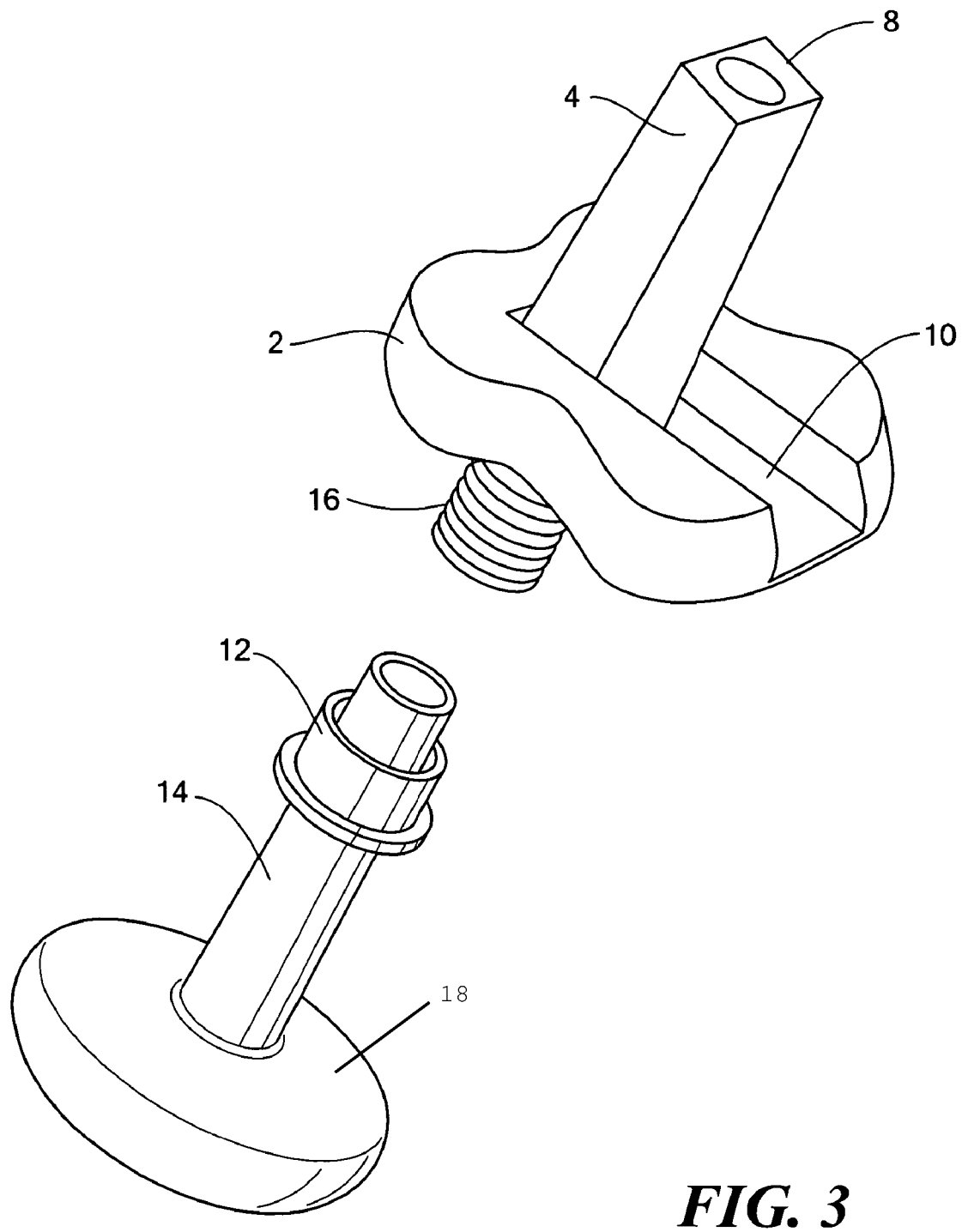
FIG. 3 is an exploded view showing the device with a novel connecting apparatus.

The lumen is connected to the bottom of the bolster. FIG. 2. When the connecting member is rotated 90°, so that it is in the position as shown in FIG. 3, a direct access or opening is available from an upper end of the connecting end, through the connecting member, and into the bolster, through the lower opening of the bolster, and into the lumen. When the connecting member is rotated to the position shown in FIG. 2, the connecting member blocks the opening to the bolster, also blocking access to the lumen.

As shown, a channel is formed in the bolster. The connecting member is held within the channel, so that the connecting member can be fully rotated 90°. The end of the connecting member extends beyond the end of the bolster. Since the sides of the connecting member are solid and non-porous, as the connecting member is rotated to the position as shown in FIG. 2, it blocks the opening to the bolster, preventing access to the lumen.

In use, the device is connected to a lumen. A novel method and device for connecting the lumen is discussed hereinafter.

The device is connected to the lumen at the bottom opening of the bolster; an upper end of the connecting member is connected to a feeding tube, syringe, or similar supply conduit. The connecting member is formed to accept appropriate connections. After the feeding tube, syringe or other conduit is connected, the connecting member is rotated to the position shown in FIG. 3. The device is now in the open or active position, with an unobstructed conduit available from the supply source through the device and into the lumen and interior anchoring mechanism 18. At the end of the feeding process or other procedure, the connecting member is rotated from the position shown in FIG. 3, to the position shown in FIG. 2, and the supply conduit is removed. The device remains in the position as shown in FIG. 2 until access to the stomach is again required for feeding, administering medicines, evacuating the stomach, or the performance of other procedures.

The bolster is designed to lie flat against the stomach, so that it is not subject to hooking or snagging or other interaction which could present a hazard to the patient. Similarly, the connecting member is retained within a channel 10 in the bolster, so that the connecting member is not subject to hooking or snagging.

A novel means of connecting the lumen is also presented. Most tubes or conduits used with feeding tubes in the prior art are formed of silicone. Silicone is an appropriate material from which form the lumen which is used as the feeding tube. However, certain problems are also present when silicone tubes are used. Silicone tubes tend to have a low coefficient of friction, and are particularly slippery when operating in the wet conditions normally encountered with feeding tubes. Silicone tubes will tend to slip back into the stomach, which can present significant problems for the patient. The tube may not completely slip into the stomach, but it may slip far enough so that the stomach acids are introduced into the body, which can cause sepsis and other problems.

In the present invention, a collar 12 is formed having an inside diameter which is approximately the same size as, or perhaps or slightly smaller than, the outside diameter of the resilient tube 14 which is used as the feeding tube. The fit should be such that the collar can be forced onto the tube by manual pressure, but it will not readily slide. The diameter is also such that the collar does not compress to interfere with the flow of material through the tube.

The collar should either have threads, or a series of peaks and valleys, or similar irregular shape formed on the inside diameter. For example, a nut of the appropriate inside diameter could be used. Threaded, stainless steel nuts are appropriate candidates for forming the collar. As shown in FIG. 3, the fitting 16 on the bottom of the device has male threads. The outside diameter of this fitting is preferred to be slightly larger than the inside diameter of the lumen, so that the male threads are engaged with the lumen, and the fitting is advanced by threading it into the lumen.

The male threads are used as a mandrel to force the tubing into the threads or other peaks and valleys which are formed in the collar. Threads of the fitting of the device do not engage the threads of the collar. It is not necessary that the collar be threaded per se, it is only necessary that the collar have an irregular surface such as peaks and valleys which will engage and grip the silicone, or other material from which the lumen is formed, when forced against the collar by the male threads. Accordingly, the tubing which forms the lumen does not hold the fitting in place by the engagement of the threads, but rather, it is held in place by the forcing of the lumen material against the inside of the collar.

If a longer tube is desired, such as in nursing home use, the longer tube, may be attached to the connecting member of the bolster. If the tube clogs, it may be removed and replaced. In the prior art, clogging is relieved by replacing the entire tube in the endoscopy suite.

The connecting member may be removable. Removal of the connecting member facilitates insertion of laparoscopic or endoscopic instruments. Gastric or esophageal therapy may be performed, and the pivotal connector subsequently replaced. The feeding tube acts as a trocar for laproscopic surgery requiring gastric access.

What is claimed is:

1. A device for insertion into a body cavity to selectively transport fluids to and from said body cavity, comprising:
    a tube comprising a proximal end, a distal end, and a lumen which traverses from an interior of said body cavity to an exterior of said body cavity;
    an anchoring device that is attached to the proximal end of said tube, wherein said anchoring device comprises a housing, and an elongated connecting member having a lumen extending from a first end of said elongated connecting member to a second end of said elongated connecting member, said elongated connecting member being pivotally mounted to said housing, wherein said elongated connecting member is pivotable to a first position to align said lumen of said elongated connecting member with said lumen of said tube to facilitate transportation of fluids to and from said body cavity, and said elongated connecting member is alternately pivotable to a second position to prevent alignment of said lumen of said elongated connecting member with said lumen of said tube holding mechanism to prevent transportation of fluids to and from said body cavity; and
    an interior holding mechanism that is attached to the distal end of said tube,
    wherein said housing of said anchoring device comprises a channel therein, and wherein, when said elongated connecting member is in the second position, said elongated connecting member rests in said channel.

2. A device for insertion into a body cavity to selectively transport fluids to and from said body cavity as described in claim 1, wherein, when said elongated connecting member is in the second position, said elongated connecting member covers an opening of said lumen of said tube.

3. A device for insertion into a body cavity to selectively transport fluids to and from said body cavity as described in claim 2, wherein, when said elongated connecting member is in the second position and said elongated connecting member covers an opening of said lumen of said tube, said elongated connecting member extends beyond an end of said housing.

4. A device for insertion into a body cavity to selectively transport fluids to and from said body cavity as described in claim 1, wherein said tube is formed of a resilient material, and further comprising a fitting that extends from a side of said anchoring device that is opposite said elongated connecting member, said fitting having threads that engage an interior of said tube, said tube having a collar positioned on a upper end thereof, said collar having an irregular shape which engages an exterior of said tube, wherein said fitting forces said tube against said collar to hold said tube in place relative to said anchoring device.

5. A device for insertion into a body cavity to selectively transport fluids to and from said body cavity as described in claim 4, wherein said collar is a nut, and wherein said irregular shape is provided by threads formed in said nut.

6. A device for insertion into a body cavity to selectively transport fluids to and from said body cavity as described in claim 1, wherein said anchoring device is attached to said proximal end of said tube by:
 a fitting having threads on a distal end that engage an interior of said proximal end of said tube, and
 a collar positioned around the proximal end of said tube, said collar having an irregular shape which engages an exterior of said tube,
 wherein said fitting forces said tube against said collar to hold said tube in place relative to said fitting.

7. A device for insertion into a body cavity to selectively transport fluids to and from said body cavity as described in claim 6, wherein said collar is a nut, and wherein said irregular shape is provided by threads formed in said nut.

8. A device for insertion into a body cavity to selectively transport fluids to and from said body cavity as described in claim 1, wherein, when said elongated connecting member is in the second position, said elongated connecting member extends beyond an end of said housing.

9. A method of selectively transporting fluids to and from a body cavity of a patient, comprising:
 inserting a device into the stomach of a patient, said device comprising:
  a tube comprising a lumen which traverses from an interior of said body cavity to an exterior of said body cavity;
  an anchoring device that is attached to said tube on the exterior of the body cavity, wherein said anchoring device comprises a housing and an elongated connecting member having a lumen extending from a first end of said elongated connecting member to a second end of said elongated connecting member, said housing being shaped to lie flat against a patient, said elongated connecting member being pivotally mounted to said housing to permit movement between a first position in which said elongated connecting member is positioned substantially parallel to said tube to align said lumen of said elongated connecting member with said lumen of said tube to permit transportation of fluids to and from said body cavity and a second position in which said elongated connecting member is positioned substantially perpendicular to said tube to prevent alignment of said lumen of said elongated connecting member with said lumen of said tube to prevent transportation of fluids to and from said body cavity; and
  an interior anchoring mechanism attached to said tube on the interior of the body cavity.

10. The method as claimed in claim 9 wherein said tube is a feeding tube.

11. The method as claimed in claim 10 wherein said feeding tube is a gastrostomy feeding tube.

12. The method as claimed in claim 9 wherein said tube has a first end and a second end, said second end having an enlargement for anchoring said second end of said tube within a body cavity, said anchoring device being attached to said first end of said tube.

13. The method as claimed 9, wherein, when said elongated connecting member is positioned to prevent alignment of said lumen of said elongated connecting member with said lumen of said tube, said elongated connecting member extends beyond an end of said housing.

14. The method as claimed in claim 9, wherein said housing of said anchoring device comprises a channel therein, and wherein, when said elongated connecting member is positioned to prevent alignment of said lumen of said elongated connecting member with said lumen of said tube, said elongated connecting member rests in said channel and extends beyond an end of said channel.

15. The method as claimed in claim 9, further comprising delivering fluids to the body cavity via the tube.

16. The method as claimed in claim 9, further comprising removing fluids from the body cavity via the tube.

* * * * *